United States Patent [19]

Göhde et al.

[11] 4,021,117

[45] May 3, 1977

[54] PROCESS FOR AUTOMATIC COUNTING AND MEASUREMENT OF PARTICLES

[76] Inventors: Hildegard Göhde; Wolfgang Göhde, both of v.-Stauffenberg-Str. 40, 4400 Munster, Germany

[22] Filed: Aug. 7, 1975

[21] Appl. No.: 602,750

[52] U.S. Cl. .......................... 356/39; 250/222 PC; 324/71 CP; 235/92 PC; 356/102

[51] Int. Cl.² ................. G01N 33/16; G01N 27/00

[58] Field of Search ................... 356/39, 102, 103; 324/71 CP; 250/222 PC; 235/92 PC

[56] References Cited

UNITED STATES PATENTS

| | | | |
|---|---|---|---|
| 3,861,800 | 1/1975 | Rapoza et al. ..................... | 356/103 |
| 3,936,741 | 2/1976 | Coulter et al. ................. | 235/92 PC |
| 3,938,038 | 2/1976 | Campbell ...................... | 324/71 CP |

Primary Examiner—Vincent P. McGraw
Attorney, Agent, or Firm—Roylance, Abrams, Berdo & Kaul

[57] ABSTRACT

A method of counting and analyzing pulses representative of characteristics of particles passing through a detector device including detecting the amplitude of each pulse, measuring the area under each pulse and above a reference level, deriving a ratio of amplitude to measured area, and determining which pulses have a ratio over a selected threshold as an indication of simultaneous passage of more than one pulse through the sensing zone of the detector device.

5 Claims, 11 Drawing Figures

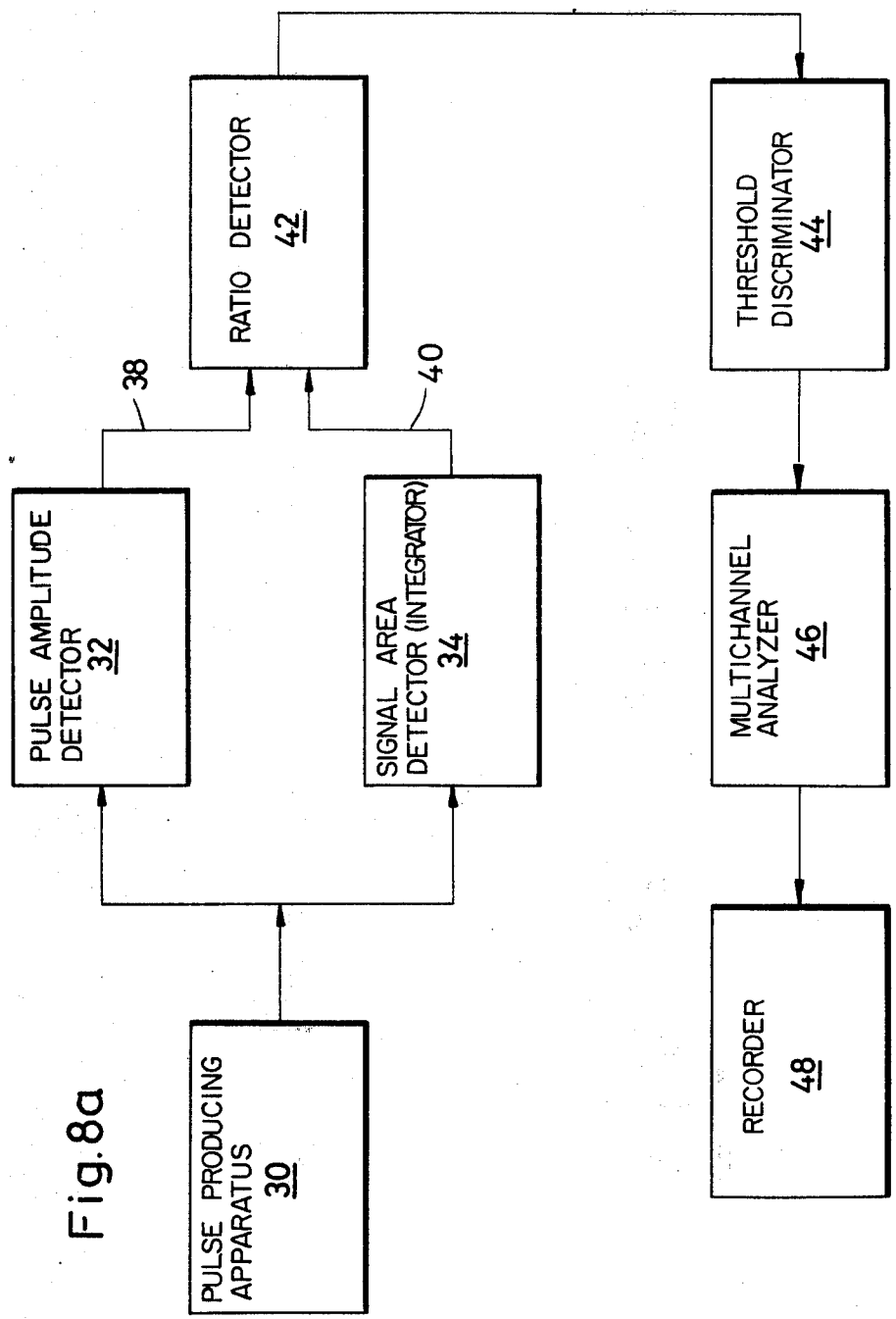

PROCESS FOR AUTOMATIC COUNTING AND MEASUREMENT OF PARTICLES

This invention relates to a process for automatic counting and measurement of particles, especially biological cells suspended in a medium that is capable of flowing, and that are carried by said medium through a defined zone of a physical field.

Various methods and correspondingly designed instruments have been used for a number of years, especially for medical diagnosis, e.g., for counting and measuring blood corpuscles, or for characterizing cells in cancer research. Methods like this can also be applied for the study of microscopically small particles, e.g., for the investigation of dust-like materials. For the sake of simplicity, however, in the following discussion reference will be limited to the study of biological particles, without thereby limiting the scope of the invention.

In all known methods of the mentioned type, there are errors in measurement caused by coincidence. If the work is done with smears of cells on object supports, there is spatial overlap. In methods of the mentioned type, for example, with so-called flow cytophotometers, or with the Coulter method, there can be temporal overlapping of the cells or of the signals that they trigger, leading to erroneous measurement signals.

In the known methods, the operating speed is limited because with increasing measurement rates there is a rise in the frequency of coincidence. Thus, in automatic counters (for example, in the Coulter method) there is a counting error, and coincidence leads to counts (particle concentrations in suspension, e.g., number of corpuscles in the blood) that are too low.

A method is known in which the pulse duration is measured in a specific partial amplitude that is referred to the maximum amplitude, and the magnitude thus obtained is used for evaluation of the pulse. This known method has the purpose of suppressing those pulses in an apparatus operating according to the Coulter method that derive from particles that have migrated outside the axial zone through the opening, and whose measured values differ from normal values delivered by particles that pass through the axial zone of the opening, because of differences in flow velocity on the one hand and field edge phenomena on the other.

Examination of signal curves taken in usual measurements has revealed that in many cases, because of the length of the measurement signal, i.e., the length of the distance between the foremost ascending slope and the last descending slope of the signal curve, one cannot clearly determine whether the signals come from one cell or a number of cells. There is a distinct probability that there is a number of cells, not just one cell, e.g., in the zone of measurement of a flow chamber, with triggering of coincidence signals. The frequency with which such errors occur is shown by the proportion of signal length to average time interval between measurement signals. With a measurement signal length of 30 $\mu$ sec, for example, and a measurement rate of 1,000 samples per second, the frequency of coincidence is 3%. Of these 3% coincidences, only a very small fraction yield wrong signals, i.e., signals of excessive amplitude. There is a false measurement signal only if the time overlap of the signals is so narrow that the sum of the individual signals representing the coincidence yields a signal that is of greater amplitude than the highest individual signal. In the detailed discussion of the invention, pictorial illustrations of this will be presented. Consideration of development of the measurement signal and of factors that affect its form leads to discussion of the way in which errors caused by coincidence can be reduced, with the same rate of measurement.

In the following discussion methods and devices will also be disclosed, by means of which coincidence can be detected in a large proportion of cases, so that they will not be carried on to registration.

The invention rests on the basic idea that in the preponderant number of cases of coincidence the signals are lengthened, as opposed to normal signals. Only in very rare instances will the cells pass through the measuring zone immediately next to each other and trigger signals that are not to be distinguished in length from signals triggered by individual cells. However, signals whose length exceeds a normal value can be detected, eliminated and, if so desired, separately counted for purposes of correcting the count, using automatically effected processes and electronic means.

However, a simple measurement of pulse length cannot be used for the detection of coincidence. If the signal length is measured at different amplifications, always at the same absolute amplitude, it appears that pulse lengths increase with increasing amplification; correspondingly, signals of different amplitudes of individual cells passing through the measurement zone are of different lengths. A coincidence signal that derives, for example, from two small measurement values cannot reliably be distinguished from a large measurement signal that derives from only one cell, by simple comparison of signal length on the basis of the signal.

The invention therefore provides that, starting from the mentioned method, for detection of coincidences, the maximum amplitude and the area between the signal curve and a line parallel to the abscissa are determined, and these two magnitudes are put in relationship to each other. The invention further provides that the signal curves for which the ratio of area to maximum amplitude exceeds a certain value are separated out as coincidences.

For different fields of application, e.g., in counting blood corpuscles, there may be provisions that the coincidence signals be counted separately, and their sum counted in with the simple sum of all signals.

In order that the manner in which the foregoing and other objects are attained in accordance with the invention can be understood in detail, particularly advantageous embodiments thereof will be described with reference to the accompanying drawings, which form a part of this specification, and wherein:

FIGS. 8a and 8b are block diagrams of two devices according to the invention in simplified form;

Figure 9:
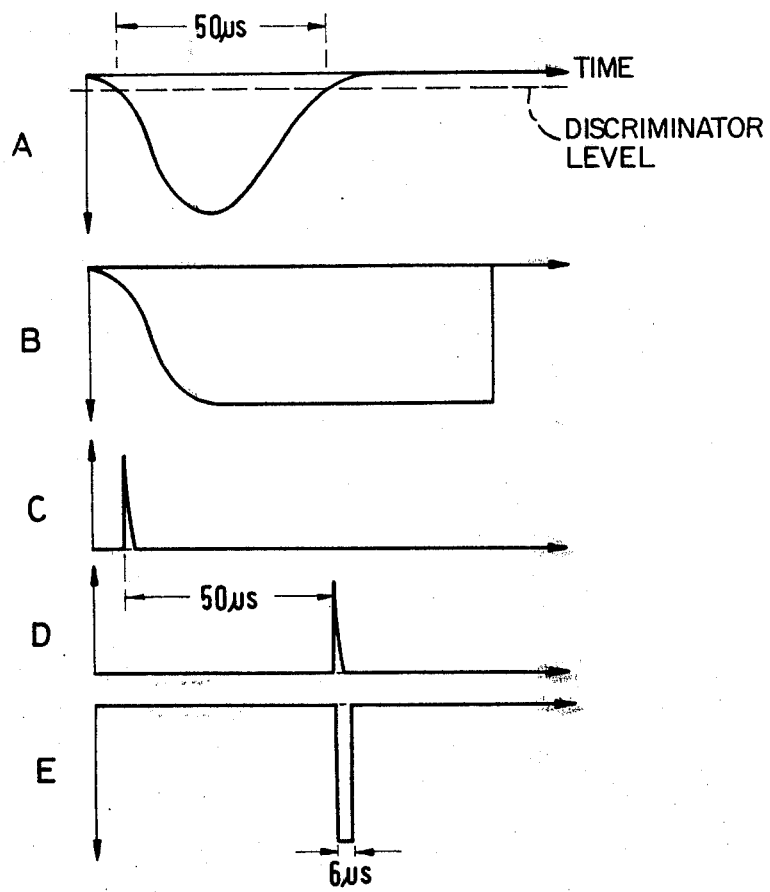
Figure 10:
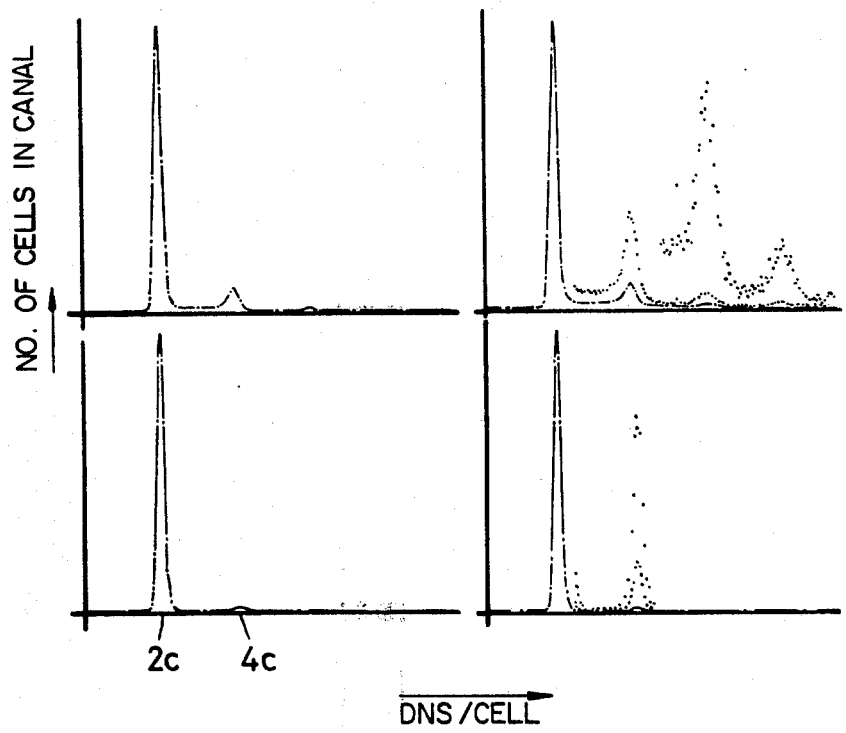

FIGS. 9A-9E are waveform diagrams of signals appearing in a peak detector used in the devices of the invention; and FIG. 10 is a set of diagrams showing a comparison of original DNS histograms of leukocytes from peripheral human blood taken at a rate of about 4,000 cells per second wherein the upper portion of the figure was taken without use of the coincidence barrier of the invention, and the lower one was taken with use of it.

The method according to the invention is described in detail below with reference to the use of a pulse cytophotometric device of the type shown in FIG. 1. Such a device promotes the formation of clearly defined conditions of observation and measurement. It is to be noted, however, that use of the process of the invention affords substantial improvements with other measuring devices also, especially those which work with changes of capacitance or resistivity to produce measurement signals.

Figure 1:
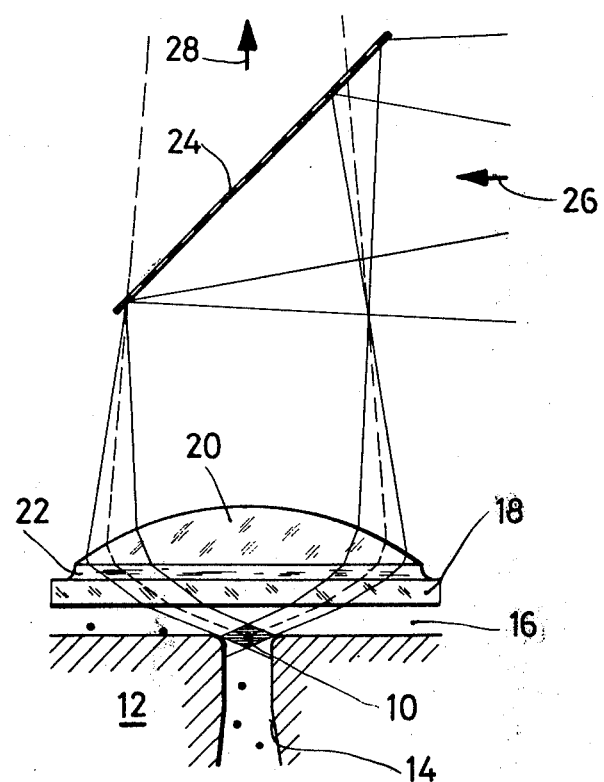
FIG. 1 is a simplified schematic representation of the measurement zone of a pulse cytophotometer usable to produce signals of the type analyzed in accordance with the present invention.

The device according to FIG. 1 has a very precisely defined zone of measurement 10, as compared to other optical measuring devices. This zone is at the entrance of a capillary canal 14 into a transverse capillary canal 16. Canals 14 and 16 are formed in a chamber 12 that substantially consists of opaque or light-impermeable material, the canal and also the zone of measurement 10 being covered by a glass plate 18. Above cover glass 18 there is an objective lens 20, with an intermediate oil immersion layer 22. The measuring zone 10 and the particles passing therethrough are illuminated by a conventional suitable light source which is not specifically shown in FIG. 1 but which produces light passing in the direction of arrow 26. This light is reflected by a partially reflective mirror 24 through objective lens 20, layer 22 and plate 18 and illuminates measuring zone 10 and the particles passing therethrough. Light is produced by, or emanates from the particles in zone 10, either as a result of reflection or fluorescence, depending upon the light source and the nature of the particles being examined. The light emanating from the particles passes back through the lens and through mirror 24 in the direction of arrow 28. The light produced by the particles is received by a conventional form of detector, not shown in FIG. 1, which responds to light impulses from the particles and produces electrical signals representative of the existence of particles in zone 10 as well as specific physical or chemical properties of the particles, e.g., particle volume, albumin content, or other characteristics. It will be recognized that the source of light and the specific nature of the detector will necessarily be a function of the kind of particles being examined and the specific characteristics which are of interest. Such devices are, however, well known and do not specifically form a part of the present invention.

Advantageously, the apparatus of FIG. 1 includes a relatively long capillary inflow canal 14 for the cell suspension so that a kind of separation of the suspension is attained in such a way that the cells pass only through the central portion of measurement zone 10. In canal 16, a particle 3 suspension fluid is fed into the canal from one end, this fluid flushing the particle-containing suspension delivered through capillary 14 away from measurement zone 10 through the opposite end of canal 16.

Turning now to the diagrams of FIGS. 2-6, the following discussions of these figures will be understood to have been made with a cell velocity at the measuring zone of an apparatus similar to FIG. 10 of about two meters per second and a plate resistance at the photomultiplier detector, receiving light passing in accordance with arrow 28, of 500 kOhm. The electrical signals produced by the photomuliplier are characterized by having a pulse width for duration at 50% of their amplitudes of about 25 $\mu$ sec long.

Figure 2:
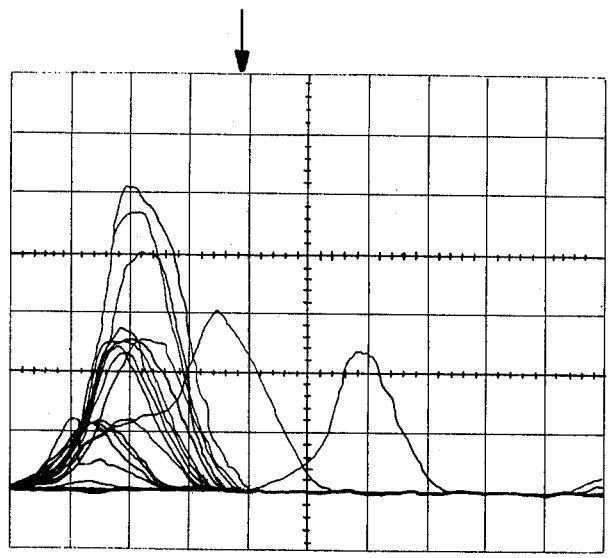
FIGS. 2 and 3 are drawings from photographs of measurement signals obtained with the device of FIG. 1 to illustrate different types of coincidence signals.
Figure 3:
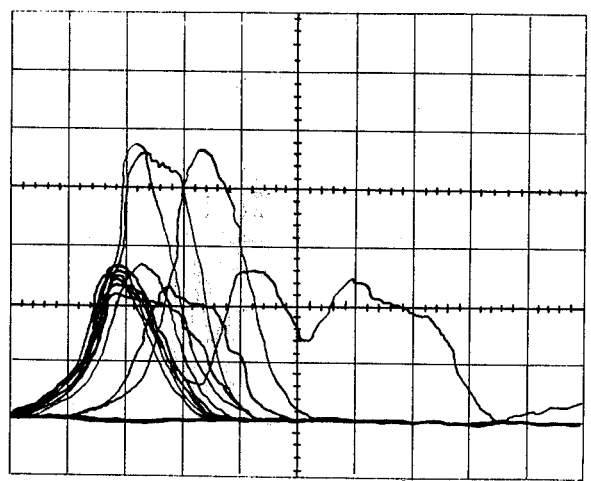

FIGS. 2 and 3 show photographs of DNS measurement signals from Ehrlich ascites tumor cells. In both figures an arrow indicates a signal which is based on coincidence. In FIG. 2 in automatic evaluation the coincidence signal simulated a measurement signal which was too high, leading to an erroneous determination. On the other hand, the coincidence signal in FIG. 3 derives from an only partially overlapping coincidence which produces no false excessively high value. In both cases (FIGS. 2 and 3) the coincidence signals are too long in relation to their maximum amplitude, which also means that the areas under the signal curves are too large with respect to the maximum amplitude of the signal.

Figure 4:
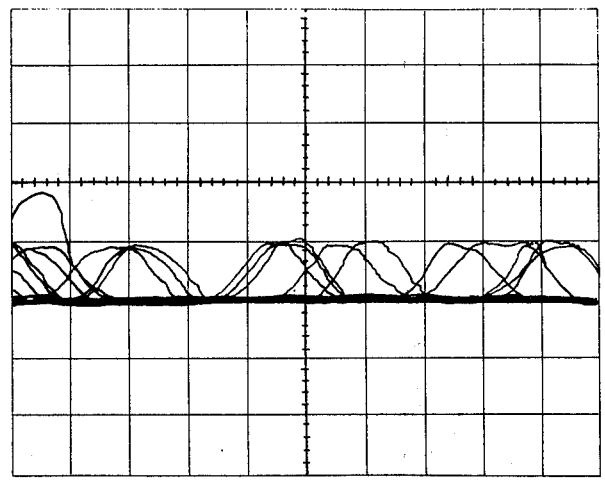
FIGS. 4–6 are drawings from photographs of measurement signals obtained with the device of FIG. 1 in various amplifications.
Figure 5:
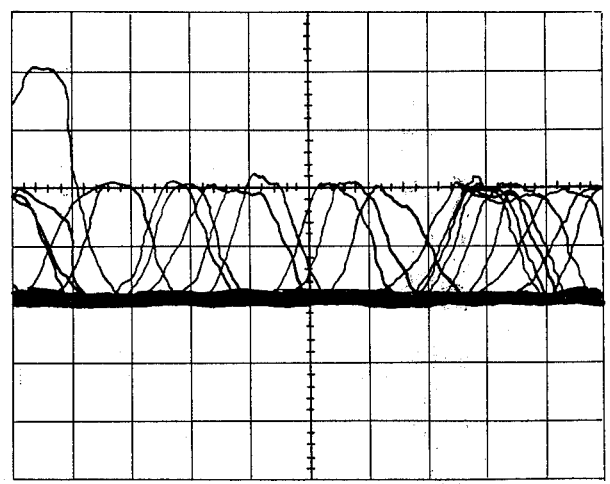
Figure 6:
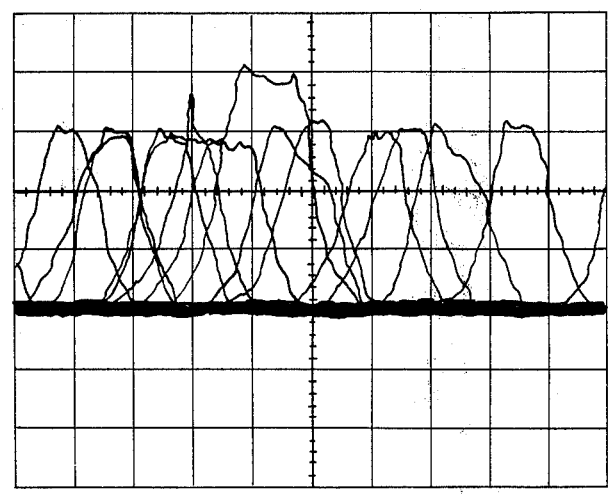

In FIGS. 4 to 6 drawings made from photographs of measurement signals with different amplifications are presented. The signals derive from human leukocytes. On the oscillograph screen one centimeter corresponds to a time of 20 $\mu$ sec.

Using the examples of FIGS. 4-6 as a basis for a description of an embodiment of the invention, a determination was made at half the amplitude of the measurement signal of the distance between the rising and descending slopes or branches (designated "length") of the signal curve, with reference to the dependence of the area below the curve upon the amplitude and length of the signal. It appeared that for all signals, independently of their amplitude, there is about the same value, in this case 25 $\mu$ sec. It therefore follows that all signals whose length at half the amplitude exceeds this value by more than a statistical fluctuation, must derive from coincidences.

Figure 7:
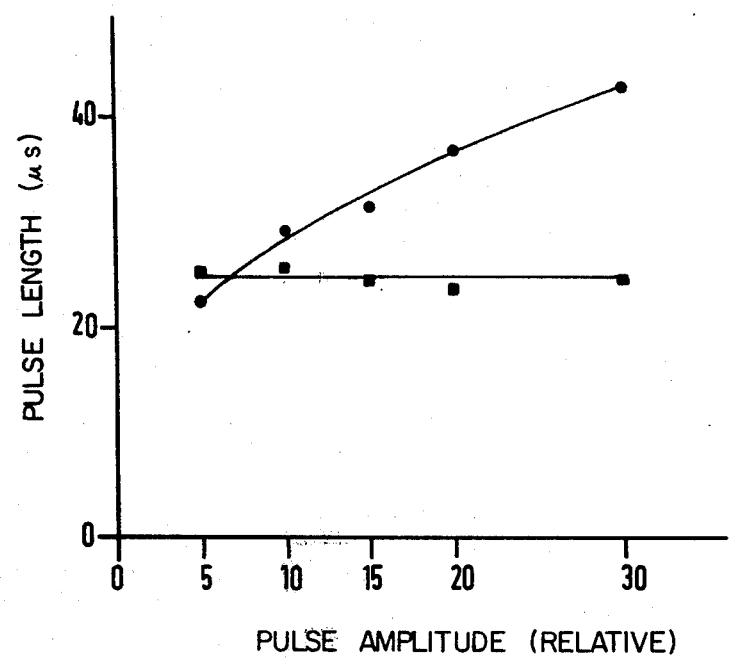
FIG. 7 is a diagram showing the dependence of pulse length upon pulse amplitude for different kinds of measurement signals.

In FIG. 7 these measured signal lengths are plotted against the amplitude of the measurement signal. The diagram was put together in such a way that the lengths of the measurement signals were determined from photographs such as those in FIGS. 4-6, at different amplifications, i.e., at different pulse amplitudes. The values plotted in FIG. 7 represent the average for 20 signals. The circles indicate pulse lengths always at the same absolute amplitude. The squares on the other hand represent the pulse lengths at different amplifications or pulse amplitudes, always at 50% of the maximum amplitude of the measurement signal in question. The diagram confirms that the pulse lengths, measured at 50% amplitude with reference to the maximum of the signal, are constant. Only coincidences such as those represented in FIG. 2 trigger longer signals. A prolongation of a signal in case of a coincidence correspondingly shows a larger area below the signal. Because of these relationships it is possible to detect and eliminate such coincidence signals in an automatic process.

Figure 8B:
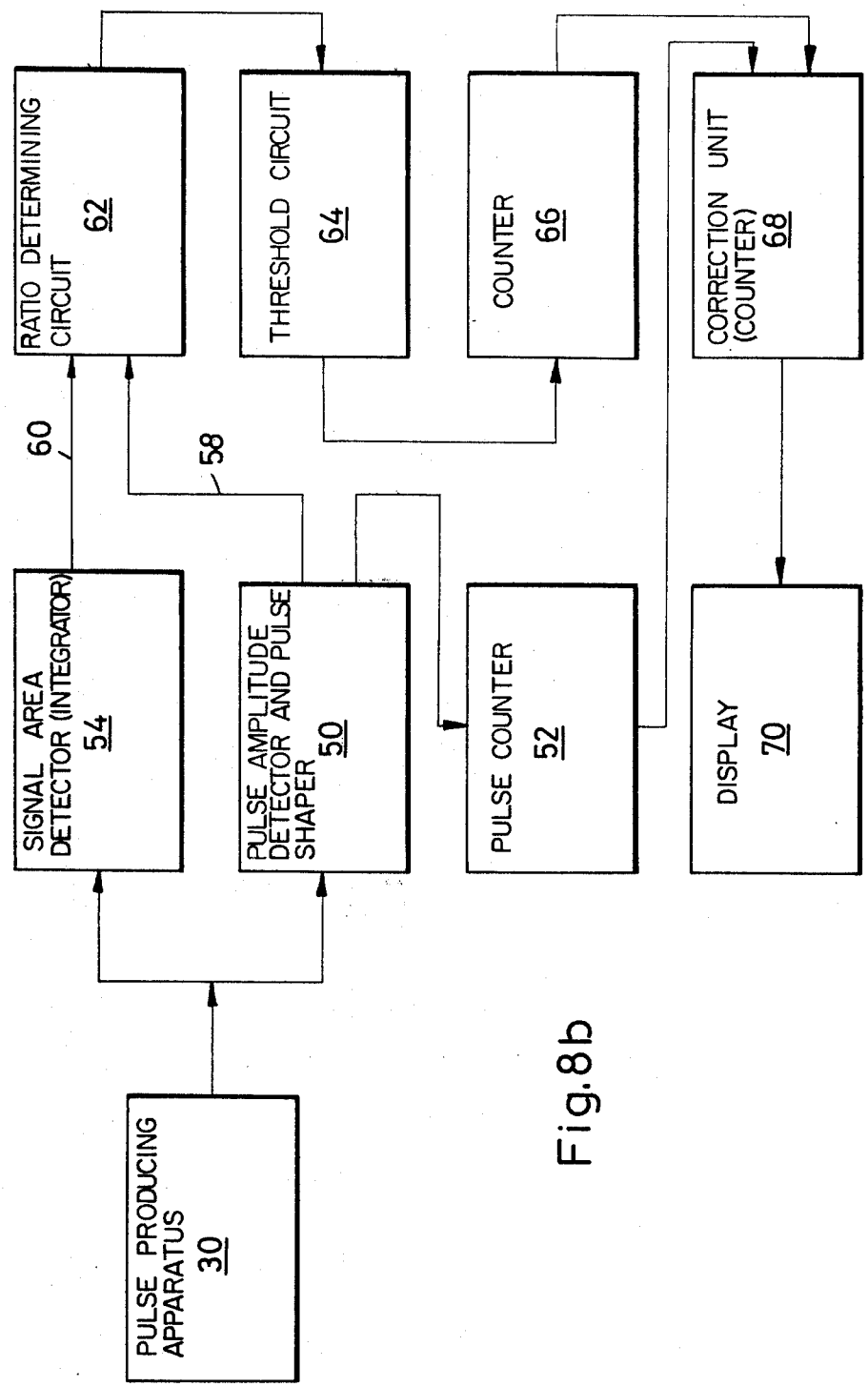

FIGS. 8a and 8b show in simplified block circuit diagrams devices for execution of the process of the invention. FIG. 9 schematically shows pulses that occur in such devices.

In the schematic representation of FIG. 8a, block 30 indicates an instrument for the production of electrical signals. This instrument can include the parts from FIG. 1 which are designated 10-25. Instead of this block 30 can also be constituted by those components of a Coulter counter which serve for immediate production of signals. For different measurements, executed with the instrument according to FIG. 1, for example, for studies on human leukocytes, it has proven useful to use the amplitude of the measurement signal as a measure for the deoxyribonucleic acid content per cell. For this purpose, see FIG. 8a, an evaluating device 32 is connected to receive the output of signal producing instrument 30, device 32 including a peak detector 32. In parallel with peak detector 32, and also receiving the output of instrument 30, there is connected a detector 34 for determination of the signal area. For this purpose, detector 34 can be an integrator. The output signals of detectors 32 and 34 are delivered via channels 38 and 40 to a circuit 42 for formation of a quotient from the values determined in devices 32 and 34. Circuit 42 can function as an analog or digital device. In the latter case channels 38 and 40 would be provided with corresponding analog/digital converters. A discriminator 44 is connected to the output of device 42. The discriminator 44 in this instrument suppresses those quotients formed from pulse amplitude and signal area that are below a determined threshold value. These quotients in which the signal area is relatively large in comparison to signal amplitude are the result of coincidences and are separated out for this reason. The rest of the signals, for which the quotients of signal amplitude and signal area are above a specific limit value, are delivered to a multichannel analyzer 46 in which the signals are classified in accordance with their maximum amplitudes. For this a control connection (not illustrated) from peak detector 32 to analyzer 46 can be provided, or device 42 can convert the pulse amplitude into a corresponding code which, in device 46, makes possible the control or piloting of the channel, corresponding to the maximum amplitude of the delivered signal. An output unit 48 is connected to multichannel analyzer 46 which can be a recording or display device such as, for example, an x–y recorder which draws the distributions of magnitude of the signals which pass the threshold of discriminator 44.

In the block diagram of FIG. 8a the parts designated 32–48 correspond to instrument part 28 of FIG. 1.

Whereas the diagram of FIG. 8a shows a general measurement device, FIG. 8b shows a device for a particle counting instrument. Block 30 has the same meaning as in FIG. 8a and may be, for example, a Coulter counter or a pulse cytophotometer. The signals produced in instrument 30 are delivered to a detector 50 for determination of pulse amplitude and this circuit can, in this case, be combined with a pulse former. A counter 52 is connected to detector 50, which element counts all signals produced in instrument 30.

Parallel to detector 50 in device 30 there is a detector 54 connected for determination of the signal area. For this determination detector 54 can also function as an ordinary integrator. Device 50 is connected via a channel 58, and device 54 via a channel 60, with a circuit 62 which forms the quotients from pulses amplitude and signal area. Parts 58, 60 and 62 correspond in construction and operation substantially to parts 38, 40 and 42 of the device according to FIG. 8a.

A discriminator 64 is connected to circuit 62, which in this case allows passage of signals whose quotients indicate coincidence, i.e., in which the signal area is relatively large in proportion to signal amplitude. Signals whose quotients indicate normal measurement results are suppressed in discriminator 64. A counter 66 is connected to discriminator 64 for the purpose of counting coincidence signals. The results from counters 52 and 66 are combined in a correction counter unit 68. The total of the coincidence signals caused by the simultaneous passage of two particles through the measurement zone is counted into the total of all signals, i.e., simple and coincidence signals, in the correction unit 68. This yields the total of particles passing through the measuring device. An indicator 70 for this corrected count is connected to correction unit 68.

For further explanation of the particle measuring device according to FIG. 8a, a pulse waveform diagram is shown in FIGS. 9A–E showing pulses which occur in the simplest arrangement in evaluation of a measurement signal, given from instrument 30 to peak detector 32, whereby the latter cooperates with the multichannel analyzer 46.

The measurement device in this example is constructed as a sample and hold circuit in which the maximum amplitude of the measurement signal (FIG. 9A) is held for a specified time (FIG. 9B). When a preselected response threshold is exceeded (FIG. 9A), an internal signal is triggered in the peak detector (FIG. 9C). A preselectable time runs from this time at the end of which a signal (FIG. 9D) is delivered to the multichannel analyzer. This signal triggers the pickup of the maximum of the held measurement signal from FIG. 9B. This short signal (FIG. 9E) whose amplitude is the maximum amplitude of the measurement signal (FIG. 9A) is taken to device 42 and used for control of the multichannel analyzer 46. Shortly thereafter the held signal in the peak detector (FIG. 9B) is extinguished so that the device is again ready to process another measurement signal. The signal (FIG. 9E) which represents the absolute amplitude of the measurement signal in question, together with the signal area, is utilized to form the relationship which, insofar as it exceeds a specific value in the form of "signal area to maximum signal magnitude," indicates and identifies the occurrence of coincidences.

In FIG. 10 there is a comparison of original frequency distributions of the DNS content of leukocytes from peripheral human blood, wherein the upper ones were taken without the coincidence threshold barrier and the lower ones with it, using a measurement rate of about 4,000 cells per second. The curves are so drawn that the abscissa shows the DNS content per cell and the ordinate shows the number of cells per channel. The high area portion under the curve at 2c stems from $G_1$ phase cells. At the top right it is further to be seen that many measurement values were recorded which preponderantly occurred from coincidences. The high proportion of these "false" values is made clear by a 4x and 16x extension of the histogram in the Y direction (see upper right) of the different curves plotted from individual points. In the upper left of FIG. 10, for clarification of the histogram reproduced upper upper right, this histogram is presented a second time without the curve portion extended in the Y direction. A close scrutiny of the measurement results which are basic to this figure shows that the signals recorded at 4c, with the minimum comparison area in 10% of their amplitude, had a length of about 40 $\mu$ sec. For taking the lower histogram, the coincidence barrier was so adjusted that only signals were plotted which were no longer than 45 $\mu$ sec in 10% of their amplitude. The histogram thus obtained shows substantially less measurement values in the region of 4c and above, where in the case of the upper histogram there were registered coincidences. Also in the region between 2c and 4c, with use of the coincidence barrier, substantially fewer cells were recorded. The histogram thus obtained, in spite of the high measurement rate, corresponds to a DNS quantity distribution of normal leukocytes of peripheral blood. In addition to a large fraction of $G_1$ phase cells (2c) and some $G_2$ phase cells (4c) there are recorded in this case less than 1% cells between 2c and 4c (S phase cells). The extension of the histogram lower right in the Y direction makes it clear that to the right of 4c no more measurement signals deriving from coincidences were recorded. Lower left, corresponding to the illustration upper left, the histogram not extended in the Y direction is plotted from the original histogram at the right.

While certain advantageous embodiments have been chosen to illustrate the invention, it will be understood by those skilled in the art that various changes and modifications can be made therein without departing from the scope of the invention as defined in the appended claims.

What is claimed is:

1. A method of automatic counting and measurement of particles, especially biological cells, suspended in a fluid medium, comprising
    passing the medium and the particles suspended therein through a physically defined zone;
    producing electrical signals having amplitudes and durations representative of characteristics of the particles passing through the zone;
    measuring the maximum amplitude of each of the signals;
    measuring the area under each of the signals and greater than a preselected level;
    determining the ratio of the measurements of maximum amplitude to area; and
    identifying those signals for which the ratio exceeds a predetermined value as being indicative of the coincidental passage of more than one particle through said zone.

2. A method according to claim 1, particularly for counting of blood corpuscles, wherein
    signals representative of coincidences are counted separately from the counting of all signals and the two counts are summed.

3. A method according to claim 1 wherein the electrical signals are produced from pulses of light produced by particles passing through a pulse cytophotometer.

4. A process according to claim 1 wherein the electrical signals are produced by passing the particles through a capacitance sensing device.

5. A process according to claim 1 wherein the electrical signals are produced by passing the particles through a resistivity sensing device.

* * * * *